United States Patent
Old et al.

(10) Patent No.: US 7,435,746 B2
(45) Date of Patent: Oct. 14, 2008

(54) 5-THIOPIPERDINYL PROSTAGLANDIN E ANALOGS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 24 days.

(21) Appl. No.: 10/564,829

(22) PCT Filed: May 16, 2005

(86) PCT No.: PCT/US2005/017167

§ 371 (c)(1),
(2), (4) Date: Jan. 13, 2006

(87) PCT Pub. No.: WO2005/121086

PCT Pub. Date: Dec. 22, 2005

(65) Prior Publication Data

US 2006/0281713 A1    Dec. 14, 2006

Related U.S. Application Data

(60) Provisional application No. 60/577,361, filed on Jun. 4, 2004.

(51) Int. Cl.
*A61K 31/45* (2006.01)
(52) U.S. Cl. ...................... 514/327; 546/221
(58) Field of Classification Search ............ 514/22, 514/89, 317, 326; 546/22, 221, 192
See application file for complete search history.

(56) References Cited

U.S. PATENT DOCUMENTS

2003/0207925 A1* 11/2003 Cameron et al. ............ 514/365
2004/0142969 A1*  7/2004 Elworthy ..................... 514/317

OTHER PUBLICATIONS

Kass et al., Arch Ophthalmol, 2002, 120, 701-713.*

* cited by examiner

*Primary Examiner*—Janet L. Andres
*Assistant Examiner*—David E Gallis
(74) *Attorney, Agent, or Firm*—Allergan, Inc.; Martin Voet; Brent A. Johnson

(57) ABSTRACT

A compound comprising

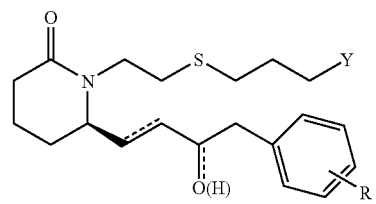

or a pharmaceutically acceptable salt or a prodrug thereof is disclosed herein. Y and R are described in detail herein A compound having an ω chain comprising

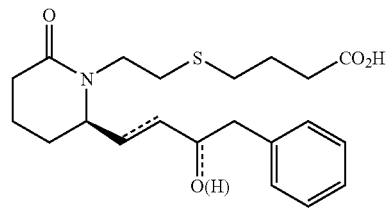

or a derivative thereof, or a pharmaceutically acceptable salt or a prodrug thereof, is disclosed. Derivatives, salts and prodrugs are identified and described in detail.

Figure 1:
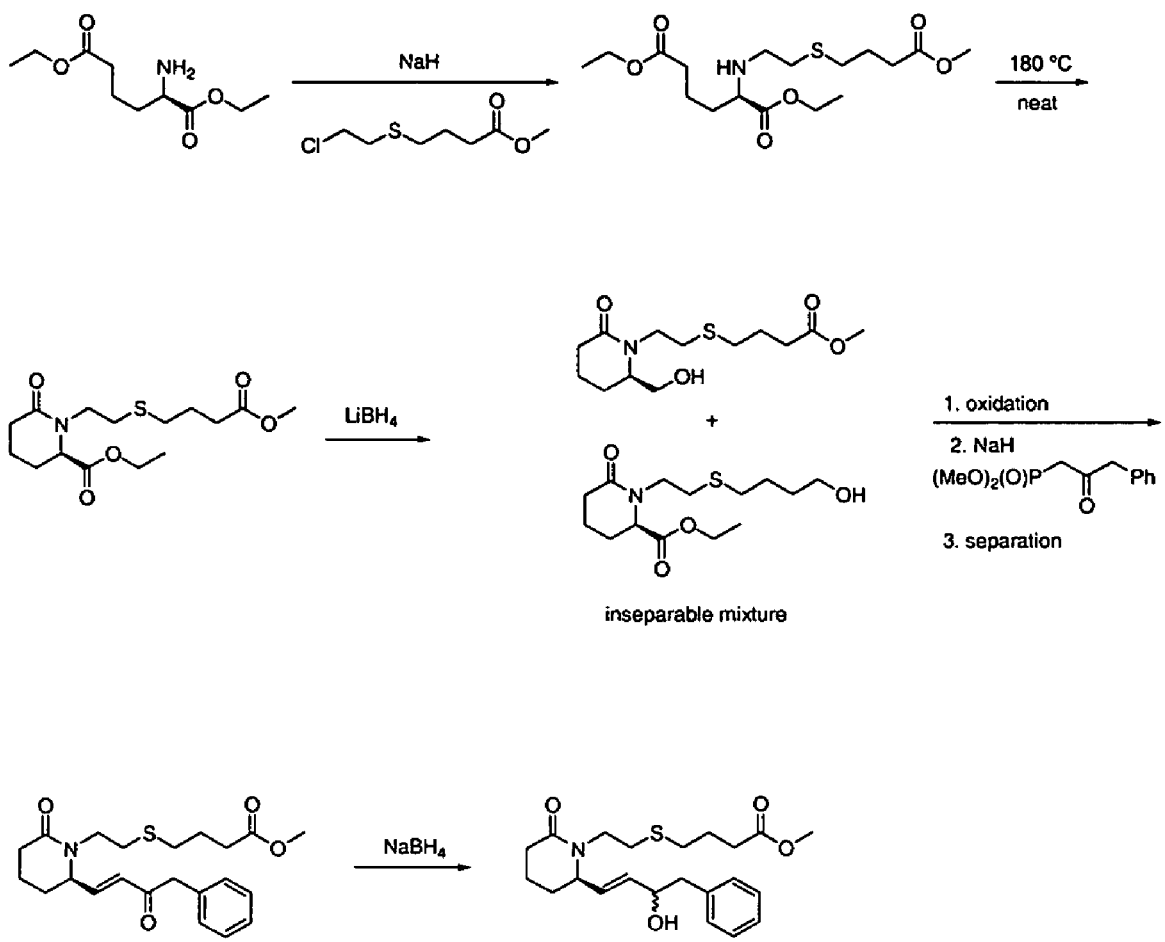

Methods of treating certain conditions or diseases, and compositions and medicaments related thereto are also contemplated.

5 Claims, 2 Drawing Sheets

5-THIOPIPERDINYL PROSTAGLANDIN E ANALOGS

CROSS REFERENCE TO RELATED APPLICATIONS

This is a national stage application under 35 U.S.C. § 371 of PCT application PCT/US 2005/017167, filed on May 16, 2005, which claims the benefit of Provisional Application No. 60/577,361, filed on Jun. 4, 2004.

FIELD OF THE INVENTION

This invention relates to compounds which are useful as therapeutic agents. Among other potential uses, these compounds are believed to have properties which are characteristic of prostaglandins.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives.

Prostaglandins can be described as derivatives of prostanoic acid which have the following structural formula:

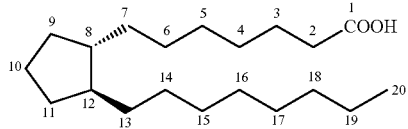

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of United States patents assigned to Allergan, Inc. prostaglandin esters with increased ocular hypotensive activity accompanied with no or substantially reduced side-effects are disclosed. Some representative examples are U.S. Pat. No. 5,446,041, U.S. Pat. No. 4,994,274, U.S. Pat. No. 5,028,624 and U.S. Pat. No. 5,034,413 all of which are hereby expressly incorporated by reference.

U.S. Pat. No. 5,688, 819, commonly assigned to Allergan, Inc., and incorporated herein by reference discloses compounds known as prostamides. Prostamides are distinguished from prostaglandins in that the oxygen which is bonded to carbonyl group is replaced by a nitrogen bearing substituent. Those skilled in the art will readily recognize that this replacement significantly alters several electronic and steric properties of an important structural feature in the biological molecule. Significantly, it is commonly believed in the art that resonance between the nitrogen lone pair and the carbonyl π-bond is significantly greater than resonance between the carbonyl group and an oxygen lone pair in a carboxylic ester or a carboxylic acid. This belief is supported by the well established experimental observation that the nitrogen atom in an amide is planar, as opposed to the pyramidal geometry of an amine. Thus, the commonly accepted belief in the art is that the nitrogen atom of an amine is $sp^3$ hybridized, while nitrogen atom of an amide is $sp^2$ hybridized, with the bonded electrons occupying the $sp^2$ hybrid orbitals and the non-bonded electron pair occupying a p orbital to allow for conjugation with the carbonyl π system. By contrast, the hybridization, bonding, and geometry of the electrons of the oxygen atom in water and alcohols are very similar to those of carboxylic acids or carboxylic esters.

The increased resonance between the nitrogen and the carbonyl group in the amide confers several unique properties to the molecule. First, it is well known in the art that hydrolysis of amides is at least two orders of magnitude slower than the hydrolysis of esters (see, for example, Francis A. Carey, Organic Chemistry, New York: McGraw-Hill Book Company, 1987, p. 779). Thus, hydrolysis of amides in vivo is slowed to such an extent that a prostamide cannot be considered to be a prodrug of a prostaglandin. Second, the increased resonance significantly increases the barrier to rotation about the nitrogen-carbonyl sigma bond relative to the analogous rotational barrier associated with esters and carboxylic acids. Thus, a prostamide has a sterically significant, stable, rigid group replacing the oxygen atom of the prostaglandin. This significant steric difference will have a significant effect in binding to a number of receptor sites since geometry is important for many receptor sites. Since the carboxylic acid group of a prostaglandin is a polar, ionizable, group, with four potential hydrogen bond receiving electron pairs, and in the case of the protonated acid, one potential hydrogen bond donor, it is reasonable for a person of ordinary skill in the art to believe that this functional group will be important to the binding of the molecule to a number of receptors. It follows that changing the resonance properties, the hybridization of the bonding and nonbonding electrons, the geometry of the nitrogen atom, the number of available hydrogen bonding sites, and the electronegativity of the of the nitrogen relative to oxygen, will confer significantly different biological properties to prostamides relative to prostaglandins.

Recently, it is becoming more commonly accepted in the art that amides have distinct properties over carboxylic acids. For example, it has been shown that anandamide, a common amide of arachidonic acid, has significant biological activity that arachidonic acid does not. Other work has also been done to show that amides have distinct activity as compared to carboxylic acid, which has caused some in the field to classify fatty acid amides as "a new family of biologically active lipids" (Bezuglov, et. al., "Synthesis and Biological Evaluation of Novel Amides of Polyunsaturated Fatty Acids with Dopamine", Bioorganic & Medicinal Chemistry Letters 11 (2001), 447-449).

It has been shown that prostamides can have pronounced effects on smooth muscle and are potent ocular hypotensive agents. Additionally, prostamides may cause significantly lower ocular surface hyperemia than prostaglandins. One prostamide exemplary of the these effects is bimatoprost, which is marketed by Allergan, Inc. under the trade name Lumigan®, which has the structure shown below.

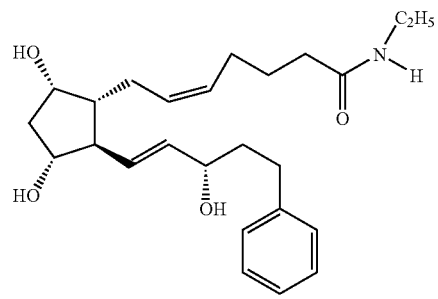

Although prostamide compounds have activity which is distinct from prostaglandins, they have many similar structural features. While not intending to be bound in any way by theory, it is believed that the structural similarity arises because prostamides are biosynthesized from N-arachidonyl ethanolamide whereas prostaglandins are biosynthesized from the structurally related arachidonic acid. Thus, they have similar structural traits, but play physiologically distinct roles due to the unique differences between the amide and the acid or ester functional groups highlighted previously. For example, it is believed that the two classes of compounds are active at distinct receptors. Thus, it is believed that the prostamide and prostaglandin receptors recognize a similar geometry in terms of the basic ring and α- and ω- chain structure, or analogs thereof, but selectively distinguish between prostaglandin and prostamide compounds based upon the nitrogen or oxygen substitution at the carbonyl group.

BRIEF DESCRIPTION OF THE INVENTION

A compound comprising

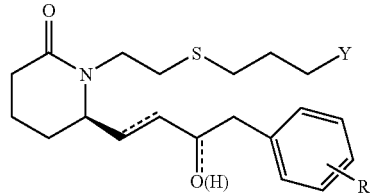

or a pharmaceutically acceptable salt or a prodrug thereof, is disclosed herein, wherein a dashed line indicates the presence or absence of a bond, and an (H) represents a hydrogen atom which is present if required by said bond;

Y is selected from the group consisting of $CO_2H$, $CONMe_2$, $CONHMe$, $CONHEt$, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

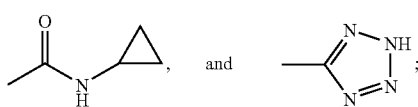

and
R is selected from the group consisting of $C_1$-$C_4$ alkyl, $C_1$-$C_4$ alkoxy, halogen, $CO_2H$, OH, COH, $COCH_3$, $COCF_3$, $NO_2$, CN, and $CF_3$.

A compound having an ω chain comprising

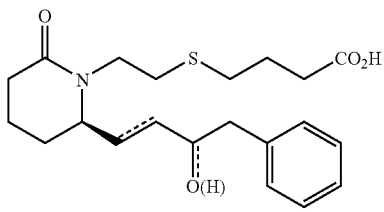

or a derivative thereof, is disclosed herein, wherein a dashed line indicates the presence or absence of a bond, and an (H) represents a hydrogen atom which is present if required by said bond;

wherein said derivative has a structure as shown above except that an alteration is made to said structure, wherein an alteration consists of a. adding, removing, or substituting a non-hydrogen atom of the ω chain;

b. converting a CO$_2$H to a moiety selected from the group consisting of CONMe$_2$, CONHMe, CONHEt, CON(OCH$_3$)CH$_3$, CONH$_2$, CON(CH$_2$CH$_2$OH)$_2$, CONH(CH$_2$CH$_2$OH), CH$_2$OH, P(O)(OH)$_2$, CONHSO$_2$CH$_3$, SO$_2$NH$_2$, SO$_2$N(CH$_3$)$_2$, SO$_2$NH(CH$_3$),

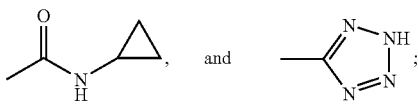

c. converting a phenyl moiety to a pyridinyl, furyl, thienyl, or n-butyl moiety, or d. adding a substituent comprising from 1 to 3 non-hydrogen atoms to a phenyl moiety;

or a pharmaceutically acceptable salt or a prodrug thereof.

Methods of treating certain conditions or diseases, and compositions and medicaments related thereto are also contemplated.

BRIEF DESCRIPTION OF THE DRAWING FIGURES

Figure 2:
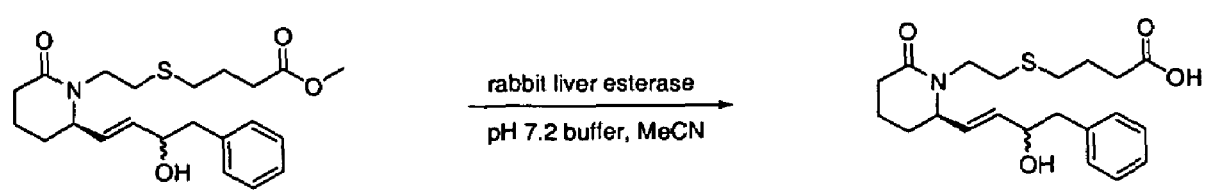

FIGS. 1 and 2 illustrate one method of preparing the compounds disclosed herein.

DETAILED DESCRIPTION OF THE INVENTION

In the structures depicted herein, a dashed line indicates the presence or absence of a bond. Thus, while not intending to be limiting, the compounds shown below are possible.

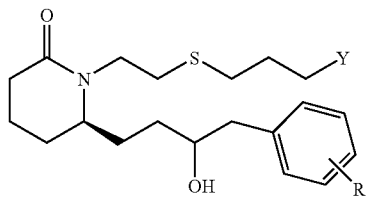

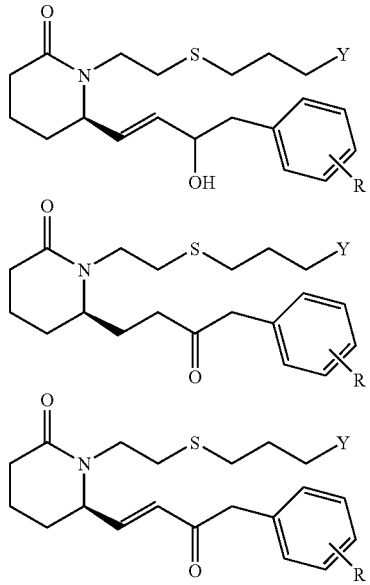

Pharmaceutically acceptable salts or prodrugs of these compounds are also considered to be useful.

Additionally, the following compounds or derivatives thereof, or pharmaceutically acceptable salts or prodrugs of these compounds or derivatives are contemplated.

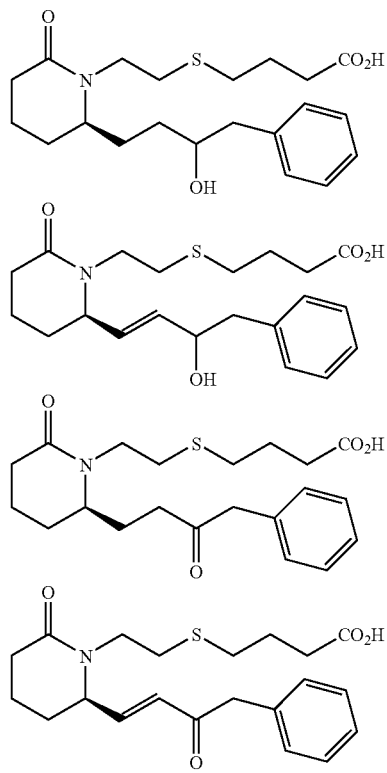

The phrase "an (H) represents a hydrogen atom which is present if required by said bond" is intended to mean that in the case that a bond indicated by a dashed line is not present, the hydrogen will be present to complete a C—OH moiety, as in some of the structures above. Alternatively if a dashed line indicates a bond which is part of a C═O moiety, no hydrogen is present.

A person of ordinary skill in the art understands the meaning of the stereochemistry associated with the hatched wedge/ solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

"$C_1$-$C_4$ alkyl" refers to any hydrocarbon having 1-4 carbon atoms and only single bonds, whether linear, branched, or cyclic, or a combination thereof. Thus, while not intending to be limiting, methyl, ethyl, propyl, isopropyl, n-butyl, isobutyl, sec-butyl, tert-butyl, cyclopropyl, cyclobutyl, methylcyclopropyl, and the like are "$C_1$-$C_4$" alkyl.

"$C_1$-$C_4$ alkoxy" refers to moiety having O directly attached to the remaining part of the molecule and to a $C_1$-$C_4$ alkyl. Thus, while not intending to be limiting, —O-methyl, —O-ethyl, —O-propyl, —O-isopropyl, —O-n-butyl, —O-isobutyl, —O-sec-butyl, —O-tert-butyl, —O-cyclopropyl, —O-cyclobutyl, —O-methylcyclopropyl, and the like are "$C_1$-$C_4$" alkoxy.

While not intending to limit the scope of the invention in any way, some compounds comprise

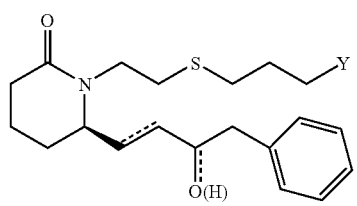

or a pharmaceutically acceptable salt or a prodrug thereof.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

While not intending to be limiting, one example of a prodrug consists of

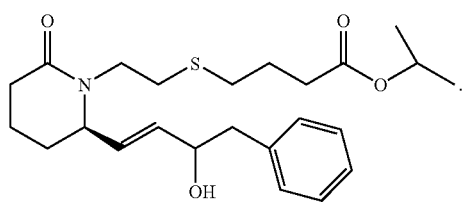

The tetrazole group,

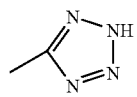

has two tautomeric forms, which can rapidly interconvert in aqueous or biological media, and are thus equivalent to one another. The tautomer of the tetrazole shown above is shown below.

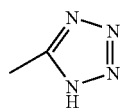

For the purposes disclosed herein, all tautomeric forms should be considered equivalent in every way.

In making reference to a derivative and alterations to a structure, it should be emphasized that making alterations and forming derivatives is strictly a mental exercise used to define a set of chemical compounds, and has nothing to do with whether said alteration can actually be carried out in the laboratory, or whether a derivative can be prepared by an alteration described. However, whether the derivative can be prepared via any designated alteration or not, the differences between the derivatives and the aforementioned structure are such that a person of ordinary skill in the art could prepare the derivatives disclosed herein using routine methods known in the art without undue experimentation.

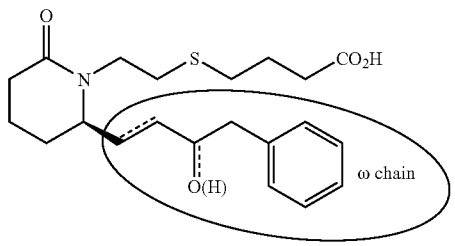

The ω chain is the group circled in the labeled structure above.

Changes to the structure can take several forms, if a non-hydrogen atom is added, the structure is changed by adding the atom, and any required hydrogen atoms, but leaving the remaining non-hydrogen atoms unchanged, such as in the two examples shown below, with the added atoms in bold type.

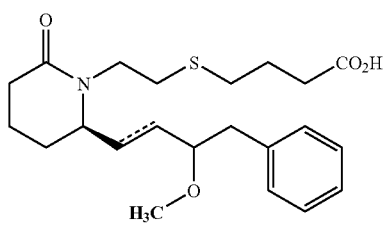

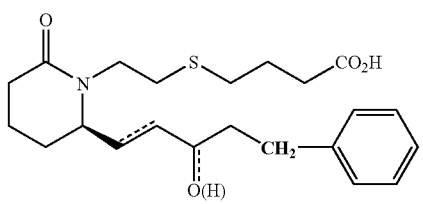

Pharmaceutically acceptable salts, tetrazoles, and prodrugs of these compounds are also contemplated.

If a non-hydrogen atom is removed, the structure is changed by removing the atom, and any required hydrogen atoms, but leaving the remaining non-hydrogen atoms unchanged, such as in the two examples shown below, with the previous location of the missing atoms indicated by arrows.

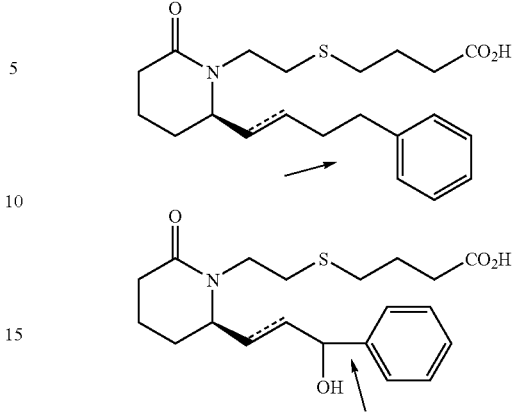

Pharmaceutically acceptable salts, tetrazoles, and prodrugs of these compounds are also contemplated.

If a non-hydrogen atom is substituted, the non-hydrogen atom is replaced by a different non-hydrogen atom, with any necessary adjustment made to the number hydrogen atoms, such as in the two examples shown below, with the substituted atoms in bold type.

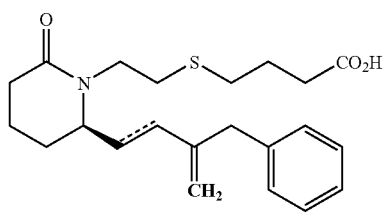

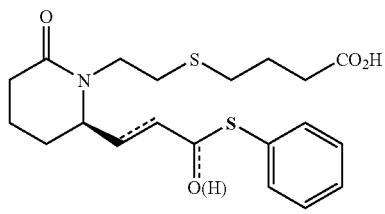

Pharmaceutically acceptable salts, tetrazoles, and prodrugs of these compounds are also contemplated.

Another alteration includes converting a $CO_2H$ to a moiety selected from the group consisting of $CONMe_2$, $CONHMe$, $CONHEt$, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

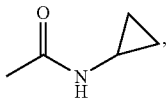 and 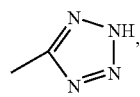

such as in the examples below.

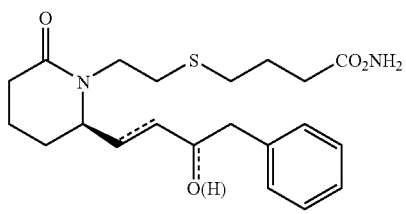

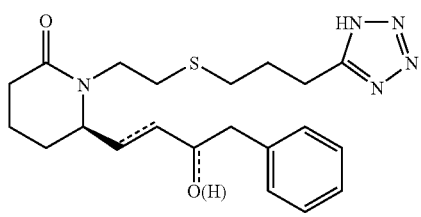

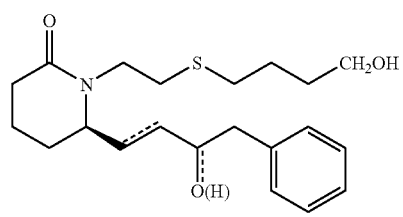

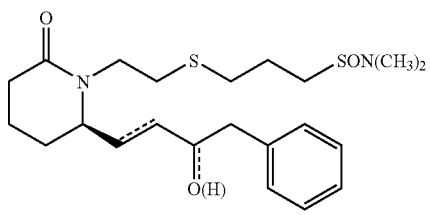

Pharmaceutically acceptable salts and prodrugs of these compounds are also contemplated.

Another alteration consists of converting a phenyl moiety to a pyridinyl, furyl, thienyl, or n-butyl moiety, such as in the examples below.

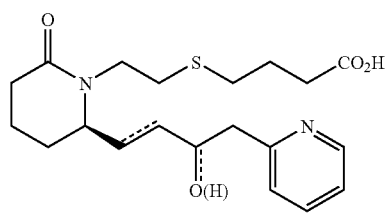

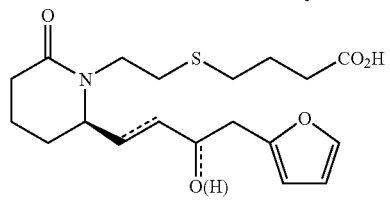

-continued

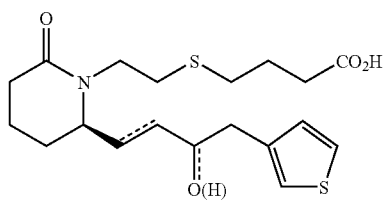

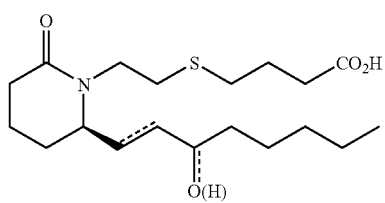

Pharmaceutically acceptable salts and prodrugs of these compounds are also contemplated.

Another alteration consists of adding a substituent comprising from 1 to 3 non-hydrogen atoms to an aromatic or a heteroaromatic ring, as in the examples below.

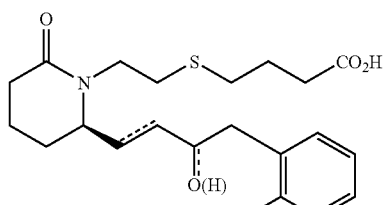

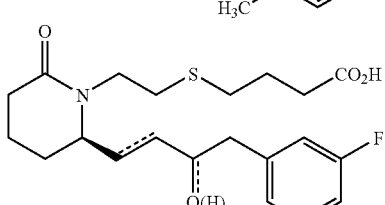

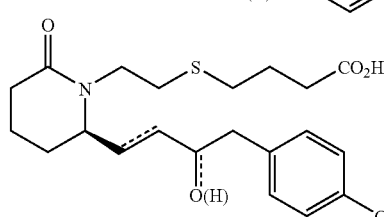

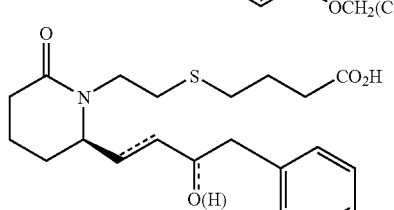

-continued

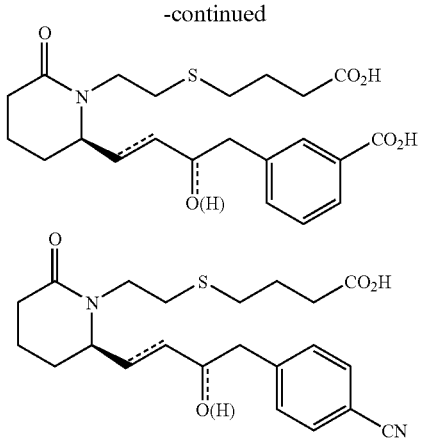

Pharmaceutically acceptable salts and prodrugs of these compounds are also contemplated.

While not intending to limit the scope of the invention, the following are examples of useful compounds 4-{2-[(R)-2-((E)-3-Hydroxy-4-phenyl-but-1-enyl)-6-oxo-piperidin-1-yl]-ethylsulfanyl}-butyric acid methyl ester, and 4-{2-[(R)-2-((E)-3-Hydroxy-4-phenyl-but-1-enyl)-6-oxo-piperidin-1-yl]-ethylsulfanyl}-butyric acid.

The compounds disclosed herein are useful for the prevention or treatment of glaucoma or ocular hypertension in mammals, or for the manufacture of a medicament for the treatment of glaucoma or ocular hypertension.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid composition which is intended for topical ophthalmic use is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric, acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

EXAMPLE 1

4-{2-[(R)-2-((E)-3-Hydroxy-4-phenyl-but-1-enyl)-6-oxo-piperidin-1-yl]-ethylsulfanyl}-butyric acid methyl ester Step 1. (R)-2-[2-(3-Methoxycarbonyl-propylsulfanyl)-ethylamino]-hexanedioic acid diethyl ester A mixture of cesium carbonate (2.71 g, 8.32 mmol) and DMF and water (10:1, 20 mL) was stirred at room temperature for 30 min before a solution of (R)-2-aminohexanedioic acid diethyl ester (prepared from D-α-aminoadipic acid according to Huang, et al., *Synth. Commun.* 1989, 19, 3485-3496, 1.80 g, 8.28 mmol) in DMF and water (10:1, 2 mL) was added via cannula. After 30 min at room temperature, potassium iodide (276 mg, 1.66 mmol) followed by 4-(2-chloroethylsulfanyl)-butyric acid methyl ester (prepared according to PCT 03/007941, 1.63 g, 8.29 mmol) in DMF and water (10:1, 5 mL) were added. After 23 h at room temperature, the reaction mixture was heated at 90° C. After 2.5 h at 90 ° C, the reaction was cooled to room temperature and saturated aqueous NaHCO$_3$ (100 mL) was added. The mixture was extracted with EtOAc (3×75 mL) and the combined extracts were washed with water (2×100 mL) and brine (2×100 mL) then dried (Na$_2$SO$_4$) filtered and concentrated in vacuo. Purification of the residue by flash column chromatography on silica gel (10%→40% EtOAc/hexane, gradient) two times afforded 893 mg (29%) of (R)-2-[2-(3-methoxycarbonyl-propylsulfanyl)-ethylamino]-hexanedioic acid diethyl ester.

Step 2. (R)-1-[2-(3-Methoxycarbonyl-propylsulfanyl)-ethyl]-6-oxo-piperidine-2-carboxylic acid ethyl ester (R)-2-[2-(3-Methoxycarbonyl-propylsulfanyl)-ethylamino]-hexanedioic acid diethyl ester (890 mg, 2.36 mmol), neat, was heated at 100° C. for 18 h. After the reaction was cooled to room temperature, TLC and $^1$H NMR analysis showed no reaction had occurred. The reaction was then heated at 180° C. After 18 h, the reaction mixture was cooled to room temperature. Purification of the residue by flash column chromatography on silica gel (25% EtOAc/hexane→EtOAc, gradient) afforded 163 mg (21%) of (R)-1-[2-(3-methoxycarbonyl-propylsulfanyl)-ethyl]-6-oxo-piperidine-2-carboxylic acid ethyl ester.

Step 3. 4-[2-((R)-2-Hydroxymethyl-6-oxo-piperidin- 1 -yl)-ethylsulfanyl]-butyric acid methyl ester Lithium borohydride (2.0 M in THF, 0.25 mL, 0.50 mmol) was added slowly to a solution of (R)-1-[2-(3-methoxycarbonyl-propylsulfanyl)-ethyl]-6-oxo-piperidine-2-carboxylic acid ethyl ester (160 mg, 0.48 mmol) in CH$_2$Cl$_2$ (1.5 mL) at −40° C. After 4.5 h at −40° C., the reaction was quenched by addition of a few drops of aqueous HCl (6 N) until gas evolution ceased. Solid NaHCO$_3$ was added and the reaction mixture was filtered and concentrated in vacuo. Purification of the residue by flash column chromatography on silica gel (CH$_2$Cl$_2$→2% MeOH/CH$_2$Cl$_2$, gradient) afforded 33 mg (~23%) of an inseparable mixture of desired product 4-[2-((R)-2-hydroxymethyl-6-oxo-piperidin-1-yl)-ethylsulfanyl]-butyric acid methyl ester and undesired product (R)-1-[2-(4-hydroxybutylsulfanyl)-ethyl]-6-oxo-piperidine-2-carboxylic acid ethyl ester.

Step 4. 4-[2-((R)-2-Formyl-6-oxo-piperidin-1-yl)-ethylsulfanyl]-butyric acid methyl ester 1-(3-(Dimethylaminopropyl)-3-ethylcarbodiimide hydrochloride (EDCI, 63 mg, 0.33 mmol) and DMSO (31 μL, 0.44 mmol) were added sequentially to a solution of the mixture of alcohols from step 3 above (30 mg, ~0.10 mmol) in benzene (1.5 mL) at 0° C. After 10 min at 0° C., pyridinium trifluoroacetate (23 mg, 0.12 mmol) was added. The reaction was allowed to warm to room temperature and then was stirred at room temperature for 2.5 h. The solution was decanted from the oily residue and the residue was washed with benzene (3×2 mL). The combined benzene phases were concentrated in vacuo to afford a crude mixture of desired product 4-[2-((R)-2-formyl-6-oxo-piperidin-1-yl)-ethylsulfanyl]-butyric acid methyl ester and undesired (R)-6-oxo-1-[2-(4-oxo-butylsulfanyl)-ethyl]-piperidine-2-carboxylic acid ethyl ester.

Step 5. 4-{2-[(R)-2-Oxo-6-((E)-3-oxo-4-phenyl-but-1-enyl)-piperidin-1-yl]-ethylsulfanyl}-butyric acid methyl ester Sodium hydride (60% dispersion in oil, 4.4 mg, 0.11 mmol) was added to a solution of dimethyl 2-oxo-3-phenyl-propylphosphonate (26.5 mg, 0.11 mmol) in THF (0.7 mL) at 0° C. After 1 h at 0° C., the mixture of aldehydes from step 4 above (~0.10 mmol) in THF (0.5 mL) was added via cannula. The reaction was allowed to warm to room temperature. After 18 h at room temperature, the reaction was quenched with aqueous acetic acid (50%, 5 mL) and extracted with EtOAc (3×5 mL). The combined organic phase was washed with brine (10 mL), dried (Na2SO$_4$), filtered and concentrated in vacuo. Purification of the residue by flash column chromatography on silica gel (20%→60% EtOAc/CH$_2$Cl$_2$, gradient) followed by preparative thin layer chromatography (silica, 5% MeOH/CH$_2$Cl$_2$) afforded 6.8 mg (16%) of 4-{2-[(R)-2-oxo-6-((E)-3-oxo-4-phenyl-but-1-enyl)-piperidin-1-yl]-ethylsulfanyl }-butyric acid methyl ester.

Step 6. 4-{2-[(R)-2-((E)-3-Hydroxy-4-phenyl-but-1-enyl)-6-oxo-piperidin-1-yl]-ethylsulfanyl}-butyric acid methyl ester Sodium borohydride (1.0 mg, 0.026 mmol), followed by MeOH (0.1 mL), was added to a solution of 4-{2-[(R)-2-oxo-6-((E)-3-oxo-4-phenyl-but-1-enyl)-piperidin-1-yl]-ethylsulfanyl}-butyric acid methyl ester (6.8 mg, 0.017 mmol) in CH$_2$Cl$_2$ (0.3 mL) at 0 ° C. After 15 min at 0° C., the reaction was quenched with aqueous HCl (0.1 M, 4 mL) and extracted with CH$_2$Cl$_2$ (3×5 mL). The combined organic phase was dried (Na$_2$SO$_4$), filtered and concentrated in vacuo to afford 6.8 mg (99%) of the title compound.

EXAMPLE 2

4-{2-[(R)-2-((E)-3-Hydroxy-4-phenyl-but-1-enyl)-6-oxo-piperidin-1-yl]-ethylsulfanyl}-butyric acid Rabbit liver esterase (134 units/mg, 1 mg) was added to a solution of 4-{2-[(R)-2-((E)-3-hydroxy-4-phenyl-but-1-enyl)-6-oxo-piperidin-1-yl]-ethylsulfanyl}-butyric acid methyl ester (5.2 mg, 0.013 mmol) in acetonitrile (0.2 mL) and pH 7.2 phosphate buffer (3.0 mL). After 24 h, acetonitrile (10 mL) was added and the reaction mixture was concentrated to dryness in vacuo. Purification of the residue by flash column chromatography on silica gel (CH$_2$Cl$_2$→5% MeOH/CH$_2$Cl$_2$, gradient) afforded 4.7 mg (94%) of the title compound.

EXAMPLE 3

The biological activity of the compounds of Table 1 may be tested using the following procedures.

Radioligand Binding

Cells Stably Expressing EP$_1$, EP$_2$, EP$_4$ and FP Receptors

HEK-293 cells stably expressing the human or feline FP receptor, or EP$_1$, EP$_2$, or EP$_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM MgCl$_2$, 2M EDTA; 10N HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H-]17-phenyl PGF$_2\alpha$(5 nM) are performed in a 100 µl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour.

[$^3$H-] PGE$_2$ (specific activity 180 Ci mmol) is used as the radioligand for EP receptors. [$^3$H] 17-phenyl PGF$_{2\alpha}$ is employed for FP receptor binding studies. Binding studies employing EP$_1$, EP$_2$, EP$_4$ and FP receptors are performed in duplicate in at least three separate experiments. A 200 µl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Competition studies are performed using a final concentration of 5 nM [$^3$H]-PGE$_2$, or 5 nM [$^3$H] 17-phenyl PGF$_{2\alpha}$ and non-specific binding determined with 10$^{-5}$M of unlabeled PGE$_2$, or 17-phenyl PGF$_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP4/Gqs5; hFP; hIP; hTP), are cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells are seeded at a density of 5×10$^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates are washed four times with HBSS-HEPES buffer to remove excess dye leaving 100 µl in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 µl volume to each well to give the desired final concentration. The peak increase in fluorescence intensity is recorded for each well. On each plate, four wells each served as negative (HBSS-HEPES buffer) and positive controls (standard agonists: BW245C (hDP); PGE$_2$ (hEP$_1$; hEP$_2$/GqS5; hEP$_{3A}$/Gqi5; hEP$_4$/Gqs5); PGF$_{2\alpha}$ (hFP); carbacyclin (hIP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of 10$^{-5}$ M. To generate concentration-response curves, four compounds per plate are tested in duplicates in a concentration range between 10$^{-5}$ and 10$^{-11}$ M. The duplicate values are averaged. In either, HTS or CoRe format each compound is tested on at least 3 separate plates using cells from different passages to give an n≧3.

The results of the activity studies presented in the table will demonstrate that the compounds disclosed herein are have activity characteristic of prostaglandins and are thus useful for the treatment of glaucoma, ocular hypertension, and other diseases or conditions related to prostaglandin activity.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound comprising

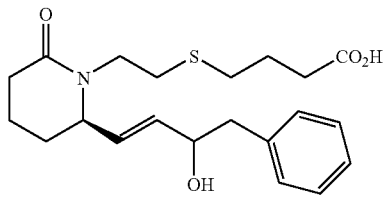

or a pharmaceutically acceptable salt or an ester thereof.

2. The compound of claim 1 consisting of

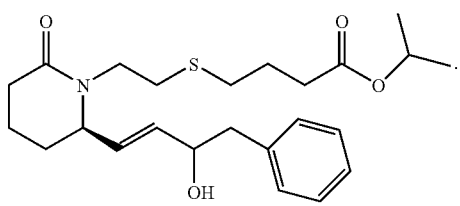

3. The compound of claim 1 comprising

4-{2-[(R)-2-((E)-3-Hydroxy-4-phenyl-but-1-enyl)-6-oxo-piperidin-1-yl]-ethylsulfanyl}-butyric acid methyl ester, or 4-{2-[(R)-2-((E)-3-Hydroxy-4-phenyl-but-1-enyl)-6-oxo-piperidin-1-yl]-ethylsulfanyl}-butyric acid, or a pharmaceutically acceptable salt or an ester thereof.

4. The compound of claim 1 consisting of

4-{2-[(R)-2-((E)-3-Hydroxy-4-phenyl-but-1-enyl)-6-oxo-piperidin-1-yl]-ethylsulfanyl}-butyric acid methyl ester, or 4-{2-[(R)-2-((E)-3-Hydroxy-4-phenyl-but-1-enyl)-6-oxo-piperidin-1-yl]-ethylsulfanyl}-butyric acid.

5. A method comprising administering an effective amount of a compound of claim 1 to a mammal, said method being effective in treating glaucoma or intraocular hypertension.

* * * * *